United States Patent [19]

Klier et al.

[11] Patent Number: 5,780,019
[45] Date of Patent: Jul. 14, 1998

[54] DEODORISING COMBINATION OF AGENTS BASED ON α-ω ALKANEDICARBOXYLIC ACIDS AND FATTY ACID PARTIAL GLYCERIDES

[75] Inventors: Manfred Klier, Aumühle; Bernd Traupe; Florian Wolf, both of Hamburg; Manfred Roeckl, Wedel, all of Germany

[73] Assignee: Beiersdorf AG, Hamburg, Germany

[21] Appl. No.: 640,881

[22] PCT Filed: Nov. 5, 1994

[86] PCT No.: PCT/DE94/01303

§ 371 Date: May 16, 1996

§ 102(e) Date: May 16, 1996

[87] PCT Pub. No.: WO95/14458

PCT Pub. Date: Jun. 1, 1995

[30] Foreign Application Priority Data

Nov. 20, 1993 [DE] Germany .................. 43 39 605.4

[51] Int. Cl.$^6$ ............ A61K 7/53; A61K 7/00; A61K 31/19

[52] U.S. Cl. ............ 424/65; 424/400; 424/401; 424/DIG. 5; 514/557; 514/558

[58] Field of Search ............ 424/65, 66, 67, 424/68, 400, 401; 514/557, 558

[56] References Cited

U.S. PATENT DOCUMENTS 4,725,431  2/1988  Hourihan et al. .......... 424/66

*Primary Examiner*—Shelley A. Dodson
*Attorney, Agent, or Firm*—Sprung Kramer Schaefer & Briscoe

[57] ABSTRACT

Cosmetic deodorants comprising mixtures of
I) α,ω-alkanedicarboxylic acids and
II) fatty acid partial glycerides of unbranched fatty acids.

10 Claims, No Drawings

DEODORISING COMBINATION OF AGENTS BASED ON α-ω ALKANEDICARBOXYLIC ACIDS AND FATTY ACID PARTIAL GLYCERIDES

The present invention relates to cosmetic active compound combinations, in particular active compound combinations as the active principle in cosmetic deodorants.

Cosmetic deodorants serve to eliminate body odour which forms when fresh perspiration, which is odourless per se, is decomposed by microorganisms. The usual cosmetic deodorants are based on various active principles.

In so-called antiperspirants, the formation of perspiration can be suppressed by astringents—chiefly aluminium salts, such as aluminium hydroxychloride (aluminium chlorohydrate). Apart from denaturing skin proteins, however, the substances used for this intervene drastically in the thermal balance of the axillary region, depending on their dosage, and should at best be used in exceptional cases.

The bacterial flora on the skin may be reduced by the use of antimicrobial substances in cosmetic deodorants. In the ideal case, only the microorganisms which cause the odour should be reduced effectively in this case. In practice, however, it has been found that the entire microflora of the skin may be impaired.

The flow of perspiration itself is not influenced by this means, and in the ideal case only microbial decomposition of the perspiration is temporarily stopped.

Combination of astringents with antimicrobially active substances in one and the same composition is also customary. However, the disadvantages of the two classes of active compound cannot be eliminated completely by this route.

Finally, body odour can also be masked by fragrances, a method which least meets the aesthetic requirements of the consumer, since the mixture of body odour and perfume fragrance tends to smell rather unpleasant.

Nevertheless, most cosmetic deodorants, like most cosmetics overall, are perfumed, even if they comprise deodorizing active compounds. Perfuming can also serve to increase consumer acceptance of a cosmetic product or to give a product a certain flair.

However, perfuming of cosmetic formulations, in particular cosmetic deodorants, comprising active compounds is not infrequently problematic, because active compounds and perfume constituents occasionally react with one another and can render one another inactive.

Deodorants should meet the following conditions:
1) They should have the effect of reliable deodorizing.
2) The natural biological processes of the skin should not be impaired by the deodorants.
3) The deodorants must be harmless in the event of an overdose or other use not as specified.
4) After repeated use, they should not become concentrated on the skin.
5) They should be easy to incorporate in customary cosmetic formulations.

Both liquid deodorants, for example aerosol sprays, roll-ons and the like, and solid formulations, for example deodorant sticks, powders, powder sprays, intimate cleansing agents and the like, are known and customary.

The object of the present invention was thus to develop cosmetic deodorants which do not have the disadvantages of the prior art. In particular, the deodorants should largely protect the microflora of the skin, but selectively reduce the number of microorganisms which are responsible for body odour.

It was also an object of the invention to develop cosmetic deodorants which are distinguished by a good skin tolerance. Under no circumstances should the deodorizing active principles become concentrated on the skin.

A further object was to develop cosmetic deodorants which harmonize with the largest possible number of customary cosmetic auxiliaries and additives, in particular with the perfume constituents which are important precisely in formulations which have a deodorizing or antiperspirant action.

Yet another object of the invention was to provide cosmetic deodorants which are active over a relatively long period of time, and in particular of the order of at least half a day, without their action decreasing noticeably.

Finally, one object of the present invention was to develop deodorizing cosmetic principles which can be incorporated as universally as possible in the most diverse presentation forms of cosmetic deodorants without being bound to one or a few specific presentation forms.

Surprisingly, it has been found, and therein lies the achievement of all these objects, that cosmetic deodorants comprising mixtures of
I) α,ω-alkanedicarboxylic acids and
II) fatty acid partial glycerides of unbranched fatty acids
remedy the disadvantages of the prior art.

Although European Patent Application Specification EP-0 036 134 describes deodorizing compositions characterized by a content of derivatives of medium- to long-chain alkanoic acids, which also include the α,ω-alkanedicarboxylic acids of the general formula

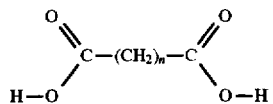

where n=4 to 10, a reference to the doctrine presented here is not to be found in this specification.

German Offenlegungsschrift DE-OS 27 03 642 furthermore describes deodorizing compositions for body hygiene which include, inter alia, certain α,ω-alkanedicarboxylic acids, but a reference to the doctrine presented here is also not to be found in this specification.

According to the invention, the α,ω-alkanedicarboxylic acids are preferably chosen from the group of substances which are described by the generic formula

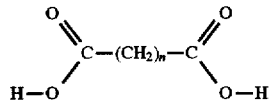

wherein n can assume numbers from 1 to 8.
n=1: Malonic acid
n=2: Succinic acid
n=3: Glutaric acid
n=4: Adipic acid
n=5: Pimelic acid
n=6: Suberic acid
n=7: Azelaic acid
n=8: Sebacic acid Partial glycerides in the context of the present invention are:
(1) Monocarboxylic acid esters of diglycerol.
(2) Monocarboxylic acid esters of triglycerol.

According to the invention, the di- and tri-glycerol units of the partial glycerides according to the invention are present as linear, unbranched molecules, that is to say "monoglycerol molecules" etherified by the particular OH groups in the 1- or 3-position.

$$\underset{\underset{HO}{|}}{H_2C}-\underset{\underset{OH}{|}}{\overset{2}{CH}}-\underset{\underset{OH}{|}}{\overset{1}{CH_2}} \quad \text{(Glycerol = "monoglycerol")}$$

A low content of cyclic di- or triglycerol units and glycerol molecules etherified by the OH groups in the 2-position can be tolerated. However, it is advantageous to keep such impurities as low as possible.

The partial glycerides according to the invention based on diglycerol are preferably monocarboxylic acid monoesters, and are preferably characterized by the following structure:

$$\underset{\underset{HO}{|}}{H_2C}-\underset{\underset{OH}{|}}{CH}-CH_2-O-CH_2-\underset{\underset{OH}{|}}{CH}-CH_2-O-\underset{\underset{O}{||}}{C}-R'$$

wherein R' is an unbranched alkyl radical having 5 to 17 C atoms.

The partial glycerides according to the invention based on triglycerol are preferably monocarboxylic acid monoesters, and are preferably characterized by the following structure:

$$\underset{\underset{HO}{|}}{H_2C}-\underset{\underset{OH}{|}}{CH}-CH_2-O-CH_2-\underset{\underset{\underset{R''-C=O}{|}}{O}}{CH}-CH_2-O-CH_2-\underset{\underset{OH}{|}}{CH}-\underset{\underset{OH}{|}}{CH_2}$$

wherein R" is an unbranched alkyl radical having 5 to 17 C atoms.

The fatty acids or monocarboxylic acids on which these esters are based are

| | | |
|---|---|---|
| hexanoic acid | (caproic acid) | (R' or R" = —$C_5H_{11}$), |
| heptanoic acid | (oenanthic acid) | (R' or R" = —$C_6H_{13}$), |
| octanoic acid | (caprylic acid) | (R' or R" = —$C_7H_{15}$), |
| nonanoic acid | (pelargonic acid) | (R' or R" = —$C_8H_{17}$), |
| decanoic acid | (capric acid) | (R' or R" = —$C_9H_{19}$), |
| undecanoic acid | | (R' or R" = —$C_{10}H_{21}$), |
| 10-undecanoic acid | (undecylenic acid) | (R' or R" = —$C_{10}H_{19}$), |
| dodecanoic acid | (lauric acid) | (R' or R" = —$C_{11}H_{23}$), |
| tridecanoic acid | | (R' or R" = —$C_{12}H_{25}$), |
| tetradecanoic acid | (myristic acid) | (R' or R" = —$C_{13}H_{27}$), |
| pentadecanoic acid | | (R' or R" = —$C_{14}H_{29}$), |
| hexadecanoic acid | (palmitic acid) | (R' or R" = —$C_{15}H_{31}$), |
| heptadecanoic acid | (margaric acid) | (R' or R" = —$C_{16}H_{33}$), |
| octadecanoic acid | (stearic acid) | (R' or R" = —$C_{17}H_{35}$), |

R' and R" are particularly advantageously chosen from the group consisting of unbranched alkyl radicals having uneven C numbers, in particular having 9, 11 and 13 C atoms.

The esters of diglycerol are in general preferable according to the invention to those of triglycerol.

Especially favourable esters are

| | | |
|---|---|---|
| diglycerol monocaprate | (DMC) | R' = 9 |
| triglycerol monolaurate | (TML) | R" = 11 |
| diglycerol monolaurate | (DML) | R' = 11 |
| triglycerol monomyristate | (TMM) | R" = 13 |

Diglycerol monocaprate (DMC) has proved to be the preferred partial glyceride according to the invention.

Partial glycerides based on those monocarboxylic acid esters which are obtainable by a process such as is described in DE-OS 38 18 293 are particularly advantageous.

According to an advantageous embodiment of the present invention, mixtures of one or more monocarboxylic acid esters of diglycerol with one or more monocarboxylic acid esters of triglycerol are used as partial glycerides of unbranched fatty acids.

According to another advantageous embodiment of the present invention, one or more monocarboxylic acid esters of diglycerol and/or one or more monocarboxylic acid esters of triglycerol in combination with other active compounds (substitute active compounds), auxiliaries, extenders and/or additives customary in cosmetics are employed as partial glycerides of unbranched fatty acids.

The extenders and/or substitute active compounds are then advantageously present in a concentration of up to 50 parts by weight, preferably up to 35 parts by weight, per 100 parts by weight of the total amount composed of the monocarboxylic acid ester or the monocarboxylic acid esters of diglycerol and/or of triglycerol and these substitute active compounds and/or extenders.

It is advantageous to choose the content of
I) α,ω-alkanedicarboxylic acids and
II) fatty acid partial glycerides of unbranched fatty acids
such that ratios of I) and II) of 5:1 to 1:5, in particular about 1:1, especially advantageously about 1:3, result.

The invention furthermore relates to a process for combatting human body odour caused by microbial decomposition of apocrine perspiration, characterized in that an active amount of mixtures of
I) α,ω-alkanedicarboxylic acids and
II) fatty acid partial glycerides of unbranched fatty acids
which can optionally be present in a suitable cosmetic carrier, is applied to the skin.

Finally, the invention also relates to the use of mixtures of
I) α,ω-alkanedicarboxylic acids and
II) fatty acid partial glycerides of unbranched fatty acids
which can optionally be present in a suitable cosmetic carrier, for combatting Gram-positive bacteria, in particular coryneform bacteria, and the use of mixtures of
I) α,ω-alkanedicarboxylic acids and
II) fatty acid partial glycerides of unbranched fatty acids
which can optionally be present in a suitable cosmetic carrier, for preventing the growth of Gram-positive bacteria, in particular coryneform bacteria.

The cosmetic deodorants according to the invention are particularly advantageously characterized in that the α,ω-alkanedicarboxylic acids are present in concentrations of 0.05–10.00% by weight, preferably 0.1–5.0% by weight, in each case based on the total weight of the formulations.

The cosmetic deodorants according to the invention are likewise particularly advantageously characterized in that the fatty acid partial glycerides of unbranched fatty acids are present in concentrations of 0.05–10.00% by weight, preferably 0.1–5.0% by weight, in each case based on the total weight of the formulations.

The cosmetic deodorants according to the invention can be in the form of aerosols, that is to say preparations which can be sprayed from aerosol containers, squeeze bottles or by a pumping device, or in the form of liquid compositions which can be applied by means of roll-on devices, as deodorant sticks and in the form of W/O or O/W emulsions, for example creams or lotions, which can be applied from normal bottles and containers. The cosmetic deodorants furthermore can advantageously be in the form of deodorizing tinctures, deodorizing intimate cleansing compositions, deodorizing shampoos, deodorizing shower or bath formulations, deodorizing powders or deodorizing powder sprays.

In addition to water, ethanol and isopropanol, glycerol and propylene glycol, customary cosmetic carriers which can be employed for preparation of the deodorizing formulations according to the invention in the ratios of amounts customary for such preparations are skin care fatty or fat-like substances, such as decyl oleate, cetyl alcohol, cetyl-stearyl alcohol and 2-octyldodecanol, as well as mucigenous substances and thickeners, for example hydroxyethyl- or hydroxypropylcellulose, and polyvinylpyrrolidone, and in addition also, in small amounts, cyclic silicone oils (polydimethylsiloxanes), as well as liquid polymethylphenylsiloxanes of low viscosity.

Propellants which are suitable for cosmetic deodorants according to the invention which can be sprayed from aerosol containers are the customary known readily volatile, liquefied propellants, for example hydrocarbons (propane, butane, isobutane), which can be employed by themselves or as a mixture with one another. Compressed air can also advantageously be used.

The expert knows of course that there are propellant gases which are non-toxic per se and would be suitable in principle for the present invention, but which nevertheless should be dispensed with because of an unacceptable action on the environment or other concomitant circumstances, in particular fluorochlorohydrocarbons (CFCs).

Emulsifiers which have proved suitable for the preparation of the cosmetic deodorants according to the invention which are advantageously to be applied to the desired areas of the skin as liquid formulations by means of a roll-on device, and which can be used in the formulations in a small amount, for example 2 to 5% by weight, based on the total composition, are nonionic types, such as polyoxyethylene fatty alcohol ethers, for example cetostearylalcohol polyethyleneglycol ether having 12 to 20 added-on ethylene oxide units per molecule, cetostearylalcohol and sorbitan esters and sorbitan esterethylene oxide compounds (for example sorbitan monostearate and polyoxyethylene sorbitan monostearate) and long-chain higher molecular weight waxy polyglycol ethers.

In addition to the constituents mentioned, perfume, dyestuffs, antioxidants (for example α-tocopherol and its derivatives or butyl hydroxytoluene (BHT=2,6-di-tert-butyl-4-methylphenol) in amounts of 0.01 to 0.03%, based on the total composition), suspending agents, buffer mixtures or other customary cosmetic bases can be added to the deodorizing cosmetic formulations according to the invention.

It is advantageous to choose the pH of the formulations according to the invention in the acid to neutral range. The pH of the formulations according to the invention is particularly advantageously chosen in the range from 4.5 to 6.5, in particular about 5.5.

The amounts of cosmetic carriers and perfume to be employed in each case can easily be determined by the expert according to the nature of the particular product by simple trial and error.

Those substances and perfume oils which are stable, do not irritate the skin and already have antibacterial or bacteriostatic properties as such are also suitable, where appropriate, for perfuming.

Apart from specific formulations which are in each case noted separately in the examples, the cosmetic formulations are prepared in the customary manner, usually by simple mixing while stirring, if appropriate with gentle heating. The preparation presents no difficulties. For emulsions, the oily phase and the aqueous phase are, for example, prepared separately, if appropriate with heating, and then emulsified.

The customary rules for compilation of cosmetic formulations, with which the expert is familiar, are otherwise to be observed.

If the compositions according to the invention are to be incorporated into powder sprays, the suspension bases for this can advantageously be chosen from the group consisting of silicic acid gels (for example those which are obtainable under the trade name Aerosil®), kieselguhr, talc, modified starch, titanium dioxide, silk powder, nylon powder, polyethylene powder and related substances.

Advantageous embodiment examples of the present invention follow. The numerical values stated always relate to % by weight, unless expressly noted otherwise.

EXAMPLES 1–4

| Pump sprays | 1 | 2 | 3 | 4 |
|---|---|---|---|---|
| a) | | | | |
| Ethanol | 69.00 | 65.00 | 65.00 | 65.00 |
| Propylene glycol | 2.00 | 2.00 | 2.00 | 2.00 |
| Ceteareth-25 ("Cremophor® A25") | 3.00 | — | — | 2.00 |
| PEG-40-hydrogenated castor oil | — | 2.50 | 2.25 | — |
| Adipic acid | 0.25 | — | — | 0.50 |
| Succinic acid | — | 0.30 | 0.40 | — |
| DMC | 0.50 | 0.50 | — | — |
| DML | — | — | 0.70 | 0.60 |
| Perfume | q.s. | q.s. | q.s. | q.s. |
| b) | | | | |
| H$_2$O, demineralised NaOH, 10% strength to pH 5.5 | in each case to 100.00 | | | |

Preparation:

The components under a) are heated, while stirring, until the mixture is present in clear molten form.

Mixture b) is prepared, after the required amount of NaOH solution to obtain a pH of about 5.5 in the finished product has been determined beforehand.

EXAMPLES 5–8

| Roll-on gels | 5 | 6 | 7 | 8 |
|---|---|---|---|---|
| a) | | | | |
| 1,3-Butanediol | 2.00 | 2.00 | 2.00 | 2.00 |
| Dipropylene glycol | 1.50 | 2.00 | 1.50 | 2.00 |
| Hydroxyethylcellulose | 0.40 | 0.40 | 0.40 | 0.40 |
| b) | | | | |
| Ethanol | 50.00 | 55.00 | 50.00 | 55.00 |
| PEG-40-hydrogenated castor oil | 2.00 | 2.00 | 1.50 | 1.50 |
| Adipic acid | 0.40 | — | 0.50 | — |
| Azelaic acid | — | 0.30 | — | 0.40 |
| DMC | 0.50 | 0.50 | — | — |
| TML | — | — | 0.90 | 0.80 |
| Perfume | q.s. | q.s. | q.s. | q.s. |
| c) | | | | |
| H$_2$O, demineralized NaOH, 10% strength to pH 5.5 | in each case to 100.00 | | | |

Preparation:

The constituents mentioned under a) are dispersed. Mixture c) is prepared, after the required amount of NaOH solution to obtain a pH of about 5.5 in the finished product has been determined beforehand, and is added to a). The mixture is allowed to swell at room temperature, and after about 15 minutes, a solution of the constituents mentioned under (b) is added. The resulting mixture is homogenized and can be transferred to bottles.

EXAMPLES 9–10

| Roll-on emulsions | 9 | 10 |
|---|---|---|
| a) | | |
| POE-21-stearyl ether ("Brij 721") | 1.50 | 1.50 |
| POE-2-stearyl ether ("Brij 72") | 2.50 | 2.50 |
| POP-15-stearyl ether ("Arlamol E") | 3.50 | 3.00 |
| Octyldodecanol | 6.00 | 6.00 |
| Methyl-paraben | — | 0.20 |
| Adipic acid | 0.50 | 0.40 |
| DMC | | |
| b) | | |
| Ethanol | 12.00 | — |
| Perfume | q.s. | q.s. |
| c) | | |
| H₂O, demineralized NaOH, 10% strength to pH 5.5 | in each case to 100.00 | |

The mixture c) is prepared, after the required amount of NaOH solution to obtain a pH of about 5.5 in the finished product has been determined beforehand.

The constituents mentioned under a) and c) are in each case heated to 75° C., while stirring. Constituents a) are then added to c).

The mixture is cooled to 35° C. A solution is prepared from constituents b) and is heated to 35° C. and added to the mixture of a) and c), while stirring.

EXAMPLES 11–12

| Wax sticks | 11 | 12 |
|---|---|---|
| Trilaurin | 37.50 | 37.50 |
| Glyceryl stearate, self-emulsifying | 10.00 | 10.00 |
| Beeswax/substitute | 24.00 | 24.00 |
| Azelaic acid | 0.60 | — |
| Adipic acid | — | 0.70 |
| DMC | 1.10 | 1.10 |
| Perfume | q.s. | q.s. |
| Caprylic/capric triglyceride | in each case to 100.00 | |

The constituents are melted at about 75° C., mixed thoroughly and poured into suitable moulds.

We claim:

1. A deodorant composition comprising a deodorizing effective amount of a combination of:
   a) an α,ω-alkanedicarboxylic acid; and
   b) a fatty acid partial glyceride of an unbranched fatty acid.

2. The deodorant composition according to claim 1, wherein the α,ω-alkanedicarboxylic acid is selected from the group consisting of malonic acid, succinic acid, glutaric acid, adipic acid, pimelic add, suberic acid, azelaic acid and sebacic acid.

3. The deodorant composition according to claim 1, wherein the fatty acid partial glyceride is selected from the group consisting of:
   a) fatty acid partial glycerides, which are monocarboxylic acid monoesters of diglycerol and have the formula:

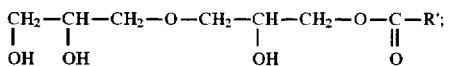

in which

R' represents an unbranched alkyl radical having 5 to 17 carbon atoms; and b) fatty acid partial glycerides, which are monocarboxylic acid monoesters of triglycerol and have the formula:

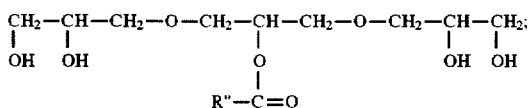

in which

R" represents an unbranched alkyl radical having 5 to 17 carbon atoms.

4. The deodorant composition according to claim 1, which comprises a deodorizing effective amount of a combination of:
   a) an α,ω-alkanedicarboxylic acid; and
   b) a fatty acid partial glyceride of an unbranched fatty acid, said fatty acid partial glyceride being selected from the group consisting of diglycerol monocaprate (DMC), triglycerol monolaurate (TML), diglycerol monolaurate (DML) and triglycerol monomyristate (TMM).

5. The deodorant composition according to claim 1, which comprises 0.05 to 10.00% by weight of said α,ω-alkanedicarboxylic acid based on the total weight of the composition.

6. The deodorant composition according to claim 5, which comprises 0.1 to 5.0% by weight of said α,ω-alkanedicarboxylic acid based on the total weight of the composition.

7. The deodorant composition according to claim 1, which comprises 0.05 to 10.00% by weight of said fatty acid partial glyceride based on the total weight of the composition.

8. The deodorant composition according to claim 7, which comprises 0.1 to 5.0% by weight of said fatty acid partial glyceride based on the total weight of the composition.

9. The deodorant composition according to claim 1, which is buffered to a pH in the range of 4.5 to 6.5.

10. A method of combating body odor comprising applying to skin a deodorizing effective amount of the deodorant composition according to claim 1.

\* \* \* \* \*